(12) United States Patent
Gale et al.

(10) Patent No.: US 7,901,452 B2
(45) Date of Patent: Mar. 8, 2011

(54) METHOD TO FABRICATE A STENT HAVING SELECTED MORPHOLOGY TO REDUCE RESTENOSIS

(75) Inventors: David C. Gale, San Jose, CA (US); Bin Huang, Pleasanton, CA (US); Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 535 days.

(21) Appl. No.: 11/823,702

(22) Filed: Jun. 27, 2007

(65) Prior Publication Data

US 2009/0005860 A1 Jan. 1, 2009

(51) Int. Cl.
  *A61F 2/06* (2006.01)
  *A61L 33/00* (2006.01)
  *B27N 3/08* (2006.01)
  *B29C 33/40* (2006.01)

(52) U.S. Cl. .......... 623/1.42; 623/1.15; 623/1.44; 623/1.46; 427/2.24; 427/2.25; 264/239; 264/220

(58) Field of Classification Search .......... 623/1.15, 623/1.42–1.46; 264/239; 427/2.24, 2.25
See application file for complete search history.

(56) References Cited

U.S. PATENT DOCUMENTS

| | | | |
|---|---|---|---|
| 3,476,463 A | 11/1969 | Kreuzer | |
| 3,687,135 A | 8/1972 | Stroganov et al. | |
| 3,839,743 A | 10/1974 | Schwarcz | |
| 3,900,632 A | 8/1975 | Robinson | |
| 4,104,410 A | 8/1978 | Malecki | |
| 4,110,497 A | 8/1978 | Hoel | |
| 4,321,711 A | 3/1982 | Mano | |
| 4,346,028 A | 8/1982 | Griffith | |
| 4,596,574 A | 6/1986 | Urist | |
| 4,599,085 A | 7/1986 | Riess et al. | |
| 4,612,009 A | 9/1986 | Drobnik et al. | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén et al. | |
| 4,733,665 A | 3/1988 | Palmaz | |
| 4,739,762 A | 4/1988 | Palmaz | |
| 4,740,207 A | 4/1988 | Kreamer | |
| 4,743,252 A | 5/1988 | Martin, Jr. et al. | |
| 4,768,507 A | 9/1988 | Fischell et al. | |
| 4,776,337 A | 10/1988 | Palmaz | |
| 4,800,882 A | 1/1989 | Gianturco | |

(Continued)

FOREIGN PATENT DOCUMENTS

CN  1241442  1/2000

(Continued)

OTHER PUBLICATIONS

U.S. Appl. No. 10/317,435, filed Dec. 11, 2002, Hossainy et al.

(Continued)

*Primary Examiner* — Timothy H Meeks
*Assistant Examiner* — Cachet I Sellman
(74) *Attorney, Agent, or Firm* — Squire, Sanders & Dempsey (US) LLP (57) ABSTRACT

Methods of fabricating a stent and a stent having selected morphology on abluminal and luminal surfaces of the stent are disclosed.

14 Claims, 7 Drawing Sheets

U.S. PATENT DOCUMENTS

| | | |
|---|---|---|
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,886,870 A | 12/1989 | D'Amore et al. |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,061,281 A | 10/1991 | Mares et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,380,976 A | 1/1995 | Couch |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,486,546 A | 1/1996 | Mathiesen et al. |
| 5,500,013 A | 3/1996 | Buscemi et al. |
| 5,502,158 A | 3/1996 | Sinclair et al. |
| 5,507,799 A | 4/1996 | Sumiya |
| 5,514,379 A | 5/1996 | Weissleder et al. |
| 5,525,646 A | 6/1996 | Lundgren et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,565,215 A | 10/1996 | Gref et al. |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,603,722 A | 2/1997 | Phan et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,656,186 A | 8/1997 | Mourou et al. |
| 5,667,767 A | 9/1997 | Greff et al. |
| 5,667,796 A | 9/1997 | Otten |
| 5,670,161 A | 9/1997 | Healy et al. |
| 5,670,558 A | 9/1997 | Onishi et al. |
| 5,686,540 A | 11/1997 | Kakizawa |
| 5,693,085 A | 12/1997 | Buirge et al. |
| 5,700,286 A | 12/1997 | Tartaglia et al. |
| 5,700,901 A | 12/1997 | Hurst et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,770,609 A | 6/1998 | Grainger et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |

| Patent No. | Date | Inventor(s) |
|---|---|---|
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,606 A | 3/2000 | Frantzen |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,110,483 A | 8/2000 | Whitbourne |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,131,266 A | 10/2000 | Saunders |
| 6,150,630 A | 11/2000 | Perry et al. |
| 6,153,252 A | 11/2000 | Hossainy et al. |
| 4,776,337 A | 12/2000 | Palmaz |
| 6,156,062 A | 12/2000 | McGuinness |
| 6,159,951 A | 12/2000 | Karpeisky et al. |
| 6,160,084 A | 12/2000 | Langer et al. |
| 6,160,240 A | 12/2000 | Momma et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,260,976 B1 | 7/2001 | Endou et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,295,168 B1 | 9/2001 | Hofnagle et al. |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,475,779 B2 | 11/2002 | Mathiowithz et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,521,865 B1 | 2/2003 | Jones et al. |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,563,080 B2 | 5/2003 | Shapovalov et al. |
| 6,563,998 B1 | 5/2003 | Farah |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,582,472 B2 | 6/2003 | Hart |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,620,194 B2 | 9/2003 | Ding et al. |
| 6,626,939 B1 | 9/2003 | Burnside |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,696,667 B1 | 2/2004 | Flanagan |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B2 | 7/2004 | Hossainy et al. |
| 6,780,261 B2 | 8/2004 | Trozera |
| 6,801,368 B2 | 10/2004 | Coufal et al. |
| 6,805,898 B1 * | 10/2004 | Wu et al. ............ 427/2.25 |
| 6,818,063 B1 | 11/2004 | Kerrigan |
| 6,822,186 B2 | 11/2004 | Strassl et al. |
| 6,846,323 B2 | 1/2005 | Yip et al. |
| 6,852,946 B2 | 2/2005 | Groen et al. |
| 6,858,680 B2 | 2/2005 | Gunatillake et al. |
| 6,867,389 B2 | 3/2005 | Shapovalov et al. |
| 6,878,758 B2 | 4/2005 | Martin et al. |
| 6,891,126 B2 | 5/2005 | Matile |
| 6,899,729 B1 | 5/2005 | Cox et al. |
| 6,911,041 B1 | 6/2005 | Zscheeg |
| 6,913,762 B2 | 7/2005 | Caplice et al. |
| 6,926,733 B2 | 8/2005 | Stinson |
| 6,943,964 B1 | 9/2005 | Zhang et al. |
| 6,981,982 B2 | 1/2006 | Armstrong et al. |
| 6,981,987 B2 | 1/2006 | Huxel et al. |
| 7,022,132 B2 | 4/2006 | Kocur |
| 7,128,737 B1 | 10/2006 | Goder et al. |
| 7,163,555 B2 | 1/2007 | Dinh |
| 7,166,099 B2 | 1/2007 | Devens, Jr. |
| 7,226,475 B2 | 6/2007 | Lenz et al. |
| 7,534,448 B2 * | 5/2009 | Saltzman et al. ............ 424/417 |
| 2001/0044652 A1 | 11/2001 | Moore |
| 2002/0004060 A1 | 1/2002 | Heublein et al. |

| | | |
|---|---|---|
| 2002/0065553 A1 | 5/2002 | Weber |
| 2002/0111590 A1 | 8/2002 | Davila et al. |
| 2002/0190038 A1 | 12/2002 | Lawson |
| 2003/0033001 A1 | 2/2003 | Igaki |
| 2003/0039689 A1 | 2/2003 | Chen et al. |
| 2003/0065355 A1 | 4/2003 | Weber |
| 2003/0093107 A1 | 5/2003 | Parsonage et al. |
| 2003/0105518 A1 | 6/2003 | Dutta |
| 2003/0105530 A1 | 6/2003 | Pirhonen |
| 2003/0108588 A1 | 6/2003 | Chen |
| 2003/0153971 A1 | 8/2003 | Chandrasekaran |
| 2003/0155328 A1 | 8/2003 | Huth |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236563 A1 | 12/2003 | Fifer |
| 2004/0093077 A1 | 5/2004 | White et al. |
| 2004/0098090 A1 | 5/2004 | Williams et al. |
| 2004/0098095 A1 | 5/2004 | Burnside et al. |
| 2004/0106987 A1 | 6/2004 | Palasis et al. |
| 2004/0111149 A1 | 6/2004 | Stinson |
| 2004/0126405 A1 | 7/2004 | Sahatjian |
| 2004/0127970 A1 | 7/2004 | Saunders et al. |
| 2004/0143180 A1 | 7/2004 | Zhong et al. |
| 2004/0143317 A1 | 7/2004 | Stinson et al. |
| 2004/0167610 A1 | 8/2004 | Fleming, III |
| 2005/0004663 A1 | 1/2005 | Llanos et al. |
| 2005/0021131 A1 | 1/2005 | Venkatraman et al. |
| 2005/0087520 A1 | 4/2005 | Wang et al. |
| 2005/0111500 A1 | 5/2005 | Harter et al. |
| 2005/0147647 A1 | 7/2005 | Glauser et al. |
| 2005/0157382 A1 | 7/2005 | Kafka et al. |
| 2005/0211680 A1 | 9/2005 | Li et al. |
| 2006/0033240 A1 | 2/2006 | Weber et al. |
| 2006/0073294 A1* | 4/2006 | Hutchinson et al. ......... 428/35.7 |
| 2006/0076708 A1* | 4/2006 | Huang et al. .................. 264/239 |
| 2006/0120418 A1 | 6/2006 | Harter et al. |
| 2006/0229711 A1* | 10/2006 | Yan et al. ...................... 623/1.38 |
| 2006/0264531 A1* | 11/2006 | Zhao ............................. 523/105 |
| 2007/0231365 A1* | 10/2007 | Wang et al. .................... 424/426 |
| 2007/0293938 A1* | 12/2007 | Gale et al. ..................... 623/1.15 |
| 2007/0299510 A1* | 12/2007 | Venkatraman et al. ....... 623/1.44 |

FOREIGN PATENT DOCUMENTS

| | | |
|---|---|---|
| DE | 44 07 079 | 9/1994 |
| DE | 197 31 021 | 1/1999 |
| DE | 198 56 983 | 12/1999 |
| DE | 29724852 | 2/2005 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0583170 | 2/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0714641 | 6/1996 |
| EP | 0 842729 | 5/1998 |
| EP | 0842729 | 5/1998 |
| EP | 0 970 711 | 1/2000 |
| EP | 1210 922 | 6/2002 |
| GB | 2 247 696 | 3/1992 |
| JP | 4-33791 | 2/1992 |
| JP | 7-124766 | 5/1995 |
| JP | 10-166156 | 6/1998 |
| JP | 2003-53577 | 2/2003 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/27587 | 10/1995 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/20429 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 02/38325 | 5/2002 |
| WO | WO 03/015978 | 2/2003 |
| WO | WO 03/057075 | 7/2003 |
| WO | WO 2004/019820 | 3/2004 |
| WO | WO 2004/023985 | 3/2004 |
| WO | WO 2004/062533 | 7/2004 |
| WO | WO 2004/112863 | 12/2004 |
| WO | WO 2005/023480 | 3/2005 |

OTHER PUBLICATIONS

Acquarulo et al., *Enhancing Medical Device Performance with Nanocomposite Poly*, Med. Device Link, www.devicelink.com/grabber.php3?URL downloaded Mar. 26, 2007, 4 pgs.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Eidelman et al., *Characterization of Combinatorial Polymer Blend Composition Gradients by FTIR Microspectroscopy*, J. Res. Natl. Inst. Standards and Technol., vol. 109, No. 2, pp. 219-231 (2004).

Fan et al., *Plasma Absorption of Femtosecond Laser Pulses in Dielectrics*, J. of Heat Transfer, vol. 124, pp. 275-283 (2002).

He et al., *Assessment of Tissue Blood Flow Following Small Artery Welding with an Intraluminal Dissolvable Stent*, Microsurgery, vol. 19(3), pp. 148-152 (1999).

Hoffnagle et al., *Design and performance of a refractive optical system that converts a Gaussian to a flattop beam*, Applied Optics, vol. 39, No. 30 pp. 5488-5499 (2000).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

NanoComposix, products, www.nanocomposix.com, downloaded Mar. 26, 2007, 2 pgs.

Nanosiliver, Photocatalyst and Nanocomposite Material, http://eng.nanocomposite.net downloaded Mar. 26, 2007, 1 pg.

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Sun et al., "Inert gas beam delivery for ultrafast laser micromachining at ambient pressure", J. of Appl. Physics, vol. 89, No. 12 pp. 8220-8223 (2001).

Tamai et al., *Initial and 6-Month Results of Biodegradable Poly-l-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

von Recum et al., *Degradation of polydispersed poly(L-lactic acid) to modulate lactic acid release*, Biomaterials, vol. 16, pp. 441-445 (1995).

Zhang et al., "Single-element laser beam shaper for uniform flat-top profiles" Optics Express, vol. 11, No. 16, pp. 1942-1948 (2003).

\* cited by examiner

METHOD TO FABRICATE A STENT HAVING SELECTED MORPHOLOGY TO REDUCE RESTENOSIS

FIELD OF THE INVENTION

This invention is directed to implantable medical devices, such as a drug delivery stents.

DESCRIPTION OF THE STATE OF THE ART

Percutaneous transluminal coronary angioplasty (PTCA) is a procedure for treating heart disease. An implantable medical device is introduced into the cardiovascular system of a patient via the brachial or femoral artery. The device is advanced through the coronary vasculature until the device is positioned across the occlusive lesion.

A problem associated with the procedure includes formation of intimal flaps or torn arterial linings which can collapse and occlude the conduit after the device is implanted. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an intraluminal prosthesis, an example of which includes an expandable stent, is implanted in the lumen to maintain the vascular patency. Stents are scaffoldings, usually cylindrical or tubular in shape, functioning to physically hold open, and if desired, to expand the wall of the passageway. Typically stents are capable of being compressed for insertion through small cavities via small catheters, and then expanded to a larger diameter once at the desired location.

In treating the damaged vasculature tissue and to further fight against thrombosis and restenosis, there is a need for administrating therapeutic substances to the treatment site. For example, anticoagulants, antiplatelets and cytostatic agents are commonly used to prevent thrombosis of the coronary lumen, to inhibit development of restenosis, and to reduce post-angioplasty proliferation of the vascular tissue, respectively. To provide an efficacious concentration to the treated site, systemic administration of such medication often produces adverse or toxic side effects for the patient.

Of the various procedures used to overcome restenosis, stents have proven to be the most effective. Stents are scaffolds that are positioned in the diseased vessel segment to create a normal vessel lumen. Placement of the stent in the affected arterial segment prevents recoil and subsequent closing of the artery. Stents can also prevent local dissection of the artery along the medial layer of the artery. By maintaining a larger lumen than that created using PTCA alone, stents reduce restenosis by as much as 30%. Despite their success, stents have not eliminated restenosis entirely. Consequently, there is a significant need to improve the performance of stents, synthetic bypass grafts, and other chronic blood contacting surfaces and or devices.

With stents, the approach has been to coat the stents with various anti-thrombotic or anti-restenotic agents in order to reduce thrombosis and restenosis. For example, stents have been coated with chemical agents such as heparin, phosphorylcholine, rapamycin, and taxol, all of which appear to decrease thrombosis and/or restenosis. Although chemical agents appear to markedly reduce thrombosis in animal models in the short term, treatment with these agents appears to have no long-term effect on preventing restenosis.

One way of reducing the likelihood of restenosis is by promoting the formation of an endothelial cell layer over the stent. The endothelial cell layer is a crucial component of the normal vascular wall, providing an interface between the bloodstream and the surrounding tissue of the blood vessel wall. Endothelial cells are also involved in physiological events including angiogenesis, inflammation and the prevention of thrombosis. In addition to the endothelial cells that compose the vasculature, endothelial cells and endothelial progenitor cells circulate postnatally in the peripheral blood. Endothelial progenitor cells are believed to migrate to regions of the circulatory system with an injured endothelial lining, including sites of traumatic and ischemic injury.

Each phase of the vascular response to injury is influenced (if not controlled) by the endothelium. It is believed that the rapid re-establishment of a functional endothelial layer on damaged stented vascular segments may help prevent these potentially serious complications by providing a barrier to circulating cytokines, preventing adverse effects of a thrombus, and by the ability of endothelial cells to produce substances that passivate the underlying smooth muscle cell layer. Endothelial cell growth factors and environmental conditions in situ are therefore essential in modulating endothelial cell adherence, growth and differentiation at the site of blood vessel injury.

Accordingly, there is a need for the development of new methods for fabricating medical devices, including stents, that promote and accelerate the formation of a functional endothelium on the surface of implanted devices so that an endothelial cell layer is formed on the target blood vessel segment or grafted lumen and inhibiting neo-intimal hyperplasia. This type of device will not only reduce the risk of restenosis, but also will also reduce the risk of thromboembolic complications resulting from implantation of the device.

SUMMARY

Disclosed herein is a bioabsorbable polymer stent comprising an abluminal surface and a luminal surface, a majority of the luminal surface being substantially smooth, and a majority of the abluminal surface being rougher than the luminal surface.

Also disclosed herein is a method of fabricating a stent, the method comprising: radially expanding a bioabsorbable polymer tube such that a majority of the inner surface of the expanded tube is substantially smooth and a majority of the abluminal surface is rougher than the luminal surface; and laser cutting a stent pattern into the expanded bioabsorbable polymeric tube to fabricate a stent.

Also disclosed herein is a method of fabricating a stent, the method comprising: radially expanding a polymeric tube by increasing a pressure in the tube and heating the tube, wherein the pressure in the tube during expansion is from about 120 psi to 250 psi, and wherein the temperature of the tube during expansion is from about 200° F. to 300° F., thereby forming a tube having a substantially smooth luminal surface and a rough abluminal surface; and laser cutting a stent pattern into the expanded polymeric tube to fabricate a stent, the stent having a substantially smooth luminal surface and a rough abluminal surface.

Also disclosed herein is a method for treating a vascular disease in a lumen with a stent, the method comprising: implanting a stent having an abluminal surface and a luminal surface into the lumen, the luminal surface being substantially smooth, wherein the abluminal surface has a surface area that is greater than 1.5 times the surface area of the luminal surface.

DETAILED DESCRIPTION

Figure 1:
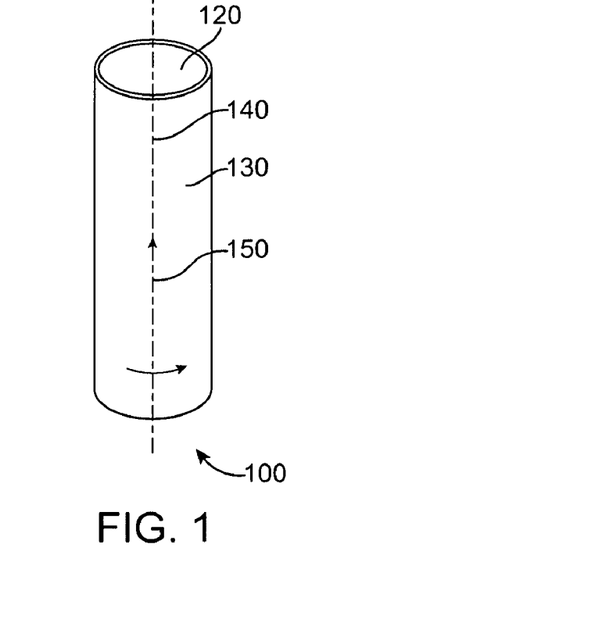
FIG. 1 depicts a tube for use in fabricating a stent, having a smooth luminal surface.

The invention provides an implantable medical device, such as a stent, methods for fabricating the medical device, and methods of treating vascular disease with the coated medical device. Some embodiments for fabricating a stent include fabricating the stent from a polymer conduit or tube. FIG. 1 depicts a tube 100 having an inside surface 120, and a surface 130, and a cylindrical axis 140 of tube 100. Polymer constructs, such as tubes, can be formed using various types of forming methods, including, but not limited to extrusion or injection molding. Representative examples of extruders include, but are not limited to, single screw extruders, intermeshing co-rotating and counter-rotating twin-screw extruders, and other multiple screw masticating extruders. Tubes fabricated from extrusion typically have smooth or relatively smooth inside and outside surfaces.

Figure 2:
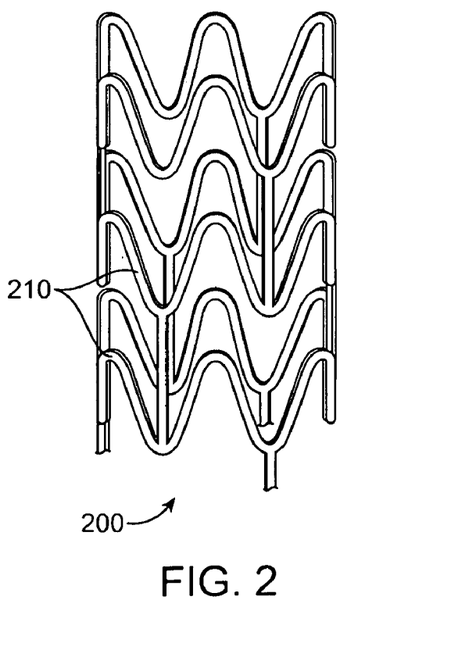
FIG. 2 is an example of a stent.

FIG. 2 depicts a three-dimensional view of a stent 200. As depicted in FIG. 2, the structure of a stent is typically composed of a scaffolding that includes a pattern or network of interconnecting structural elements often referred to in the art as struts 210 or bar arms. The pattern is not limited to the depicted stent pattern. A conventional stent is allowed to expand and contract through movement of individual structural elements of a pattern with respect to each other.

A stent such as that depicted in FIG. 2 may be formed from a polymeric tube by laser cutting a stent pattern in the tube. Representative examples of lasers that may be used include laser types such as excimer, carbon dioxide, and YAG. Chemical etching may also be used to form a pattern on the tube.

Certain embodiments of the present invention include a bioabsorbable polymer stent having a smooth or substantially smooth luminal or inside surface and an outside surface having a rough surface. More generally, embodiments of the stent of the present invention include a stent with a luminal surface smoother than an abluminal surface or a luminal surface less rough than an abluminal surface. It is believed that as a surface becomes rougher or less smooth, the degradation rate of the surface increases due to an increase in surface area. Thus, the stent of the present invention may degrade faster at the abluminal surface than the luminal surface. It is also believed that endothelialization at a surface is enhanced by surface roughness. Thus, the stent of the present invention can have increased endothelialization at an abluminal surface as compared to smooth or substantially smooth surface.

Further embodiments include fabricating a stent of the present invention. Such embodiments include fabricating a stent from a tube having an inside surface and outside surface as described above for the stent of the present invention. Additional embodiments include methods of fabricating such a tube. Other embodiments include methods of treatment of a body lumen with the stent of the present invention.

Figure 3:
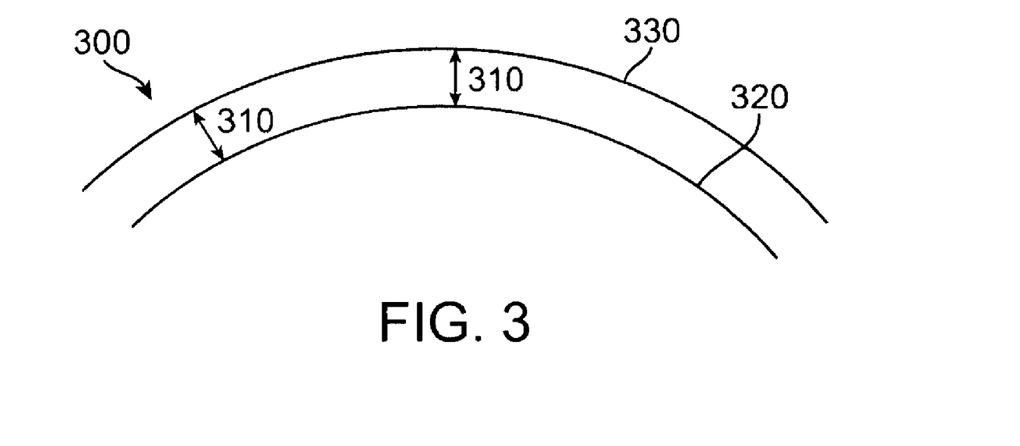
FIG. 3 depicts a cross section portion of a tube or stent strut having a substantially smooth abluminal surface and a substantially smooth luminal surface.

A "smooth surface" refers to a surface that is continuous and even. For example, a smooth surface corresponds to a mathematical representation of a surface, such as a cylindrical surface of a tube. "Substantially smooth" refers to a surface that is free or relatively free of ridges, projections, or deviations from, for example, such mathematical surface, such as a cylindrical surface. A "rough surface" refers to a surface having ridges and projections on the surface. The roughness of a surface or deviation from a smooth surface can be measured by roughness factor (rugosity) of a surface which is given by the ratio:

$$f_r = A_r/A_g$$

where $A_r$ is the real (true, actual) surface (interface) area and $A_g$ is the geometric surface (interface) area. 1986, 58, 439 IUPAC Compendium of Chemical Terminology 2nd Edition (1997). In the case of a tube, the geometric surface area is the surface area of a section of a smooth cylindrical surface and the real surface area is the actual surface area of such a section taking into account deviations from the smooth cylindrical surface due to ridges, projections, etc. Substantially smooth can refer to a surface having a roughness factor typical of a tube fabricated from extrusion. Turning to FIG. 3, depicted is a radial cross section of a portion of a tube 300 or a portion of a stent strut of a stent fabricated from such tube having a substantially smooth luminal surface 320 and a substantially smooth abluminal surface 330. The portion of tube 300 has a thickness 310, which is substantially uniform along the portion.

Figure 4:
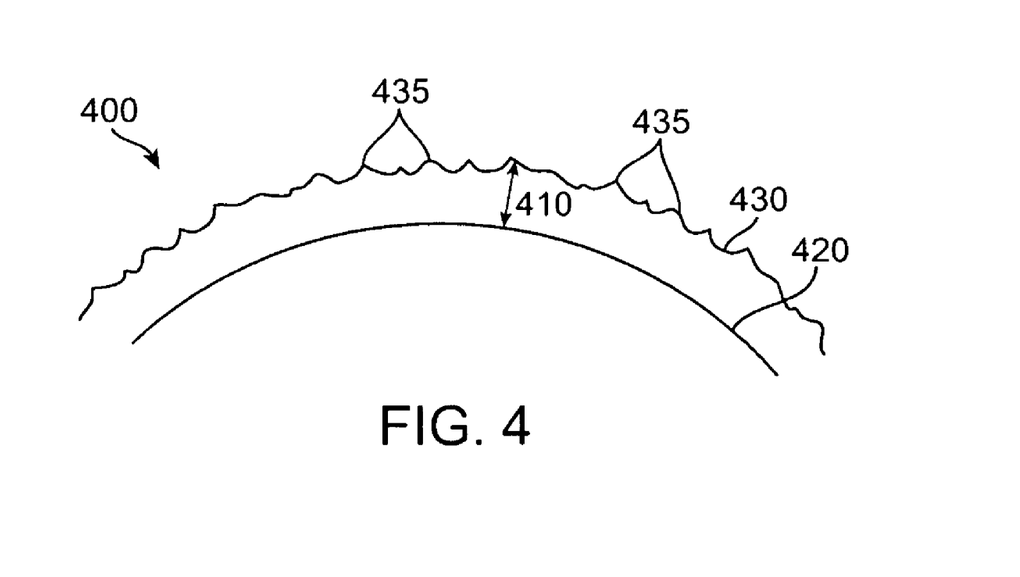
FIG. 4 depicts a cross section of a portion of a tube or stent strut having a substantially smooth abluminal surface and a rough luminal surface.

FIG. 4 depicts a radial cross section of a portion of a tube 400 or portion of a stent formed from such a tube according to one embodiment, having a substantially smooth luminal surface 420 and a rough abluminal surface 430. As shown in FIG. 4, rough abluminal surface 430 has protrusion, irregularities, or ridges 435. The roughness of abluminal surface 430 is effective to enhance the adherence or formation of endothelial cells to abluminal surface 430 which form a layer of mature endothelial cells on abluminal surface 430 of a stent. Additionally, the rough surface increases the effective surface area of abluminal surface 430 which can increase the degradation rate at abluminal surface 430. Furthermore, a smooth luminal surface 420 allows smooth blood flow through the stent with less or a reduced likelihood of turbulence.

In exemplary embodiments, the surface area of abluminal surface 430 is at least 1.5, two, or three times that of luminal surface 420 or greater than three times that of luminal surface 420. In other exemplary embodiments, the roughness factor of abluminal surface 430 is at least 1.5, two, or three times that of luminal surface 420 or greater than three time that of luminal surface 420.

In some embodiments, the rough abluminal surface may have an effective surface area for promoting or increasing the rate of cell growth or endothelialization over the abluminal surface. Without being limited by theory, it is believed that upon implantation of a stent having a rough abluminal surface 430, the cells that adhere to abluminal surface 430 transform into a mature, functional layer of endothelium on abluminal surface 430. Therefore, the roughness of abluminal surface 430 can promote cell growth by providing more surface area for cells to attach, thereby enhancing adhesion of abluminal surface 420 with the cell wall of the lumen in which the stent is implanted. The accelerated formation of the endothelial cell layer on the stent reduces the occurrence of restenosis and thrombosis at the site of implantation. In addition, it is expected that the rapid endothelialization of a biodegradable stent facilitated by rough abluminal surface 430 also accelerates the biodegradation rate of the stent.

Figure 5A:
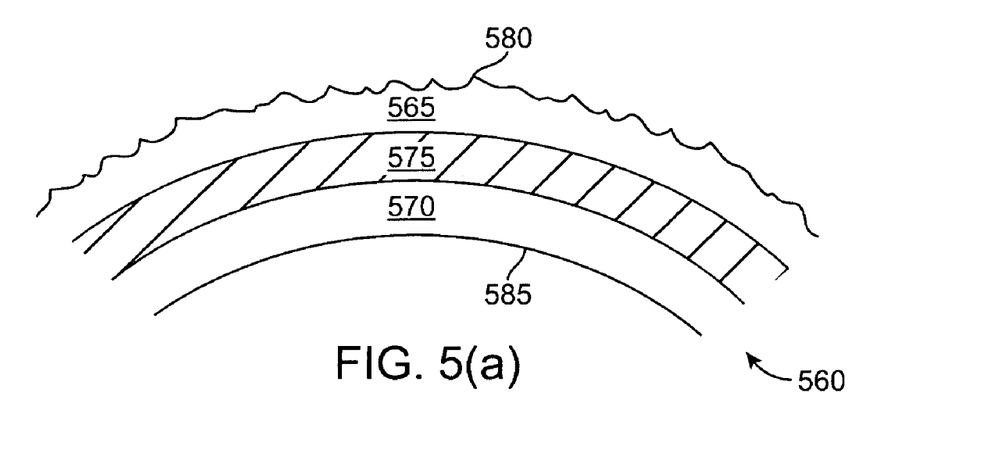
FIG. 5(a) depicts a cross section of a multilayer tube or stent strut portion.

In some embodiments, the structural elements of a stent may include two or more polymer layers, with an abluminal layer, a luminal layer, and optionally, one or more middle layers. Adjacent layers may have different properties, for example, adjacent layers can be made of different polymers. The abluminal layer can have an abluminal surface that is rough and the luminal layer can have a luminal surface is substantially smooth. Embodiments of such a stent can be formed from a tube having two or more layers with a rough outer surface and a substantially smooth inner surface. A layered tube can be formed using methods known to one of skill in art, such as by coextrusion. A rough outer surface can be formed using the blow molding process described below. FIG. 5(a) depicts a radial cross section of a portion of a layered tube 560 or portion of a stent formed from such a tube according to one embodiment. Portion 560 has an abluminal layer 565, a luminal layer 570, and a middle layer 575. Abluminal layer 565 has a rough abluminal surface 580 and luminal layer 570 has a substantially smooth luminal surface 585.

Figure 5B:
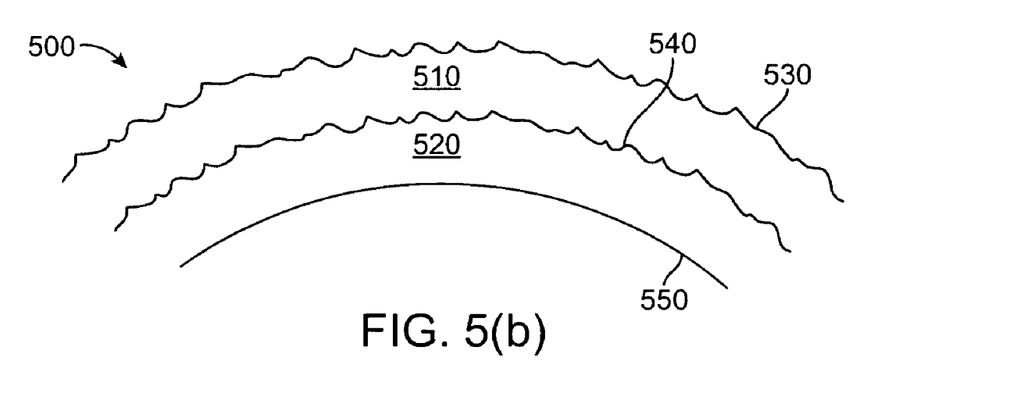
FIG. 5(b) depicts a cross section of a tube or stent strut portion having a coating deposited on a rough abluminal surface.

Additionally, in some embodiments, a rough abluminal surface can have a coating including a polymer. As depicted in FIG. 5(b), a tube portion or scaffolding portion 500 has an abluminal coating 510 that is deposited on an abluminal or outer surface 540 of tube or strut 520 Coating 510 has a rough luminal surface 530. In these embodiments, abluminal or outer surface 540 of tube or scaffolding 520 can be rough, as depicted in FIG. 5(b). An abluminal coating on a tube can be formed by applying a coating material to the outside surface of the tube using methods know to those of skill in the art such as spraying. An abluminal coating on a stent can be formed by methods such as spraying. A sheath or mask can be inserted within the stent to shield luminal surfaces from application of coating material. Luminal surface 550 of tube or scaffolding portion 520 is substantially smooth. A luminal surface 550 of portion 520 can optionally be coated, the surface of the coating having a substantially smooth surface.

Figure 6:
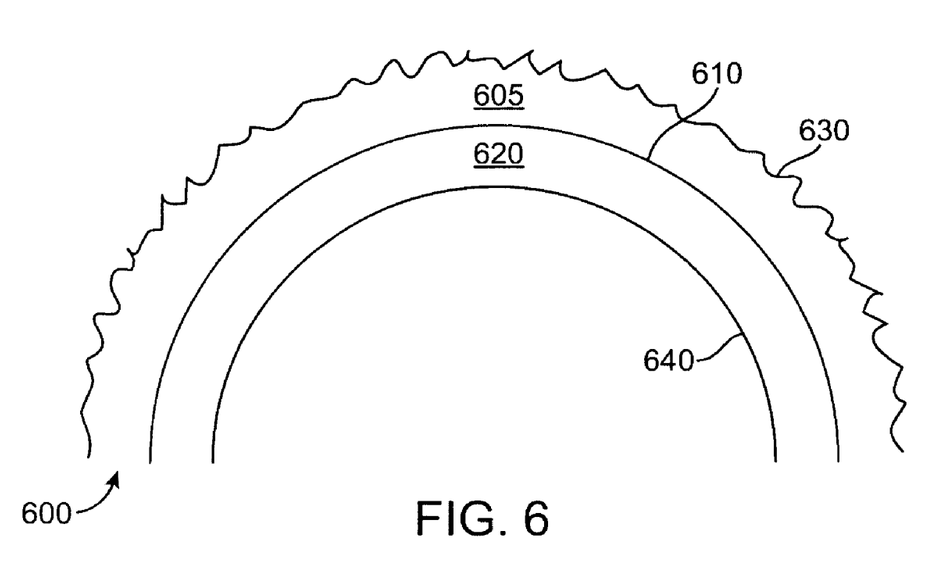
FIG. 6 depicts a cross section of a tube portion having a coating that is deposited on a rough luminal surface.

Alternatively, as depicted in FIG. 6, a coating 605 with a rough surface 630 can be deposited over an outer or a tube or scaffolding portion 620 that has a substantially smooth surface 610. Rough abluminal surface 530 in FIG. 5 or rough abluminal surface 630 in FIG. 6 facilitate the formation of an endothelial cell wall around the abluminal surface of the stent. In each of these embodiments, luminal surface 550 in FIG. 5 or luminal surface 640 in FIG. 6 are substantially smooth to assist in smooth blood flow through the lumen.

In some embodiments, the coating having a rough surface can be formed by including materials such as fibers or particulates in a coating material. The coating may be deposited on the tube prior to fabricating the stent. Alternatively, the coating may be deposited on the stent scaffolding after the tube has been laser cut to form a stent. As discussed above, a stent having the bilayer structure described above can be fabricated a polymer tube having such a structure. In certain embodiments, a tube having a bilayer structure can be formed by radially expanding a tube with blow molding. The blow molding can be performed in a manner that the expanded tube has the desired bilayer structure. In particular, the process parameters of the blow molding process can be selected to allow formation of a bilayer tube. A stent can then be formed from the expanded tube.

Furthermore, the blow molding tends to increase the radial strength of the tube and a stent fabricated from the tube. It is known that deforming a polymer construct tends to increase the strength along the axis of deformation. In particular, the radial expansion imparts strength in the circumferential direction of a tube as indicated by an arrow 150 in FIG. 1. Therefore, a radially expanded tube has a higher radial strength than an unexpanded tube. Thus, a stent fabricated from the tube has a higher radial strength.

Generally, blow molding a tube includes positioning a polymer tube in a cylindrical mold which limits the expansion of the tube. The pressure within the mold is increased, typically by blowing a gas into an open end of the tube. The tube can also be heated using various methods to facilitate the expansion. For example, a heating nozzle can blow a heated gas onto a surface of the mold at a particular axial portion of the tube. The nozzle can be translated along the length of the mold, heating the mold and tube to a selected temperature. As the nozzle translates along the length of the mold, the tube radially expands. The tube can also be heated by the gas used to increase the pressure. Additionally, the mold may be heated, for example, by heating elements on, in, and/or adjacent to the mold.

Figure 7A:
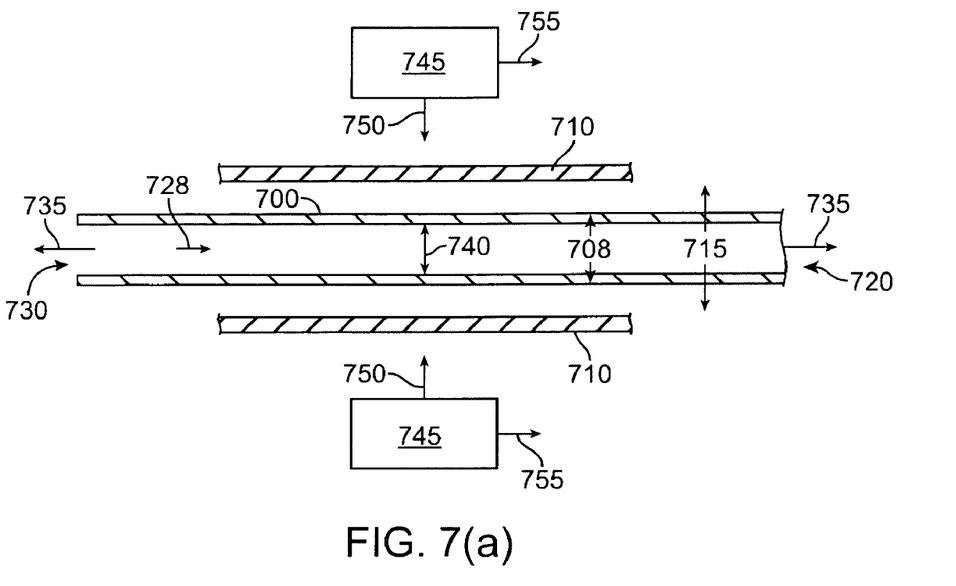
FIG. 7(a) depicts an axial, cross sectional view of a blow molding apparatus prior to radially expanding a polymeric tube.
Figure 7B:
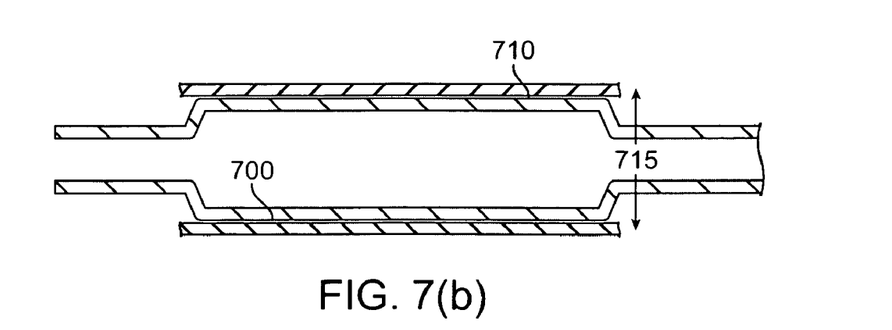
FIG. 7(b) depicts an axial, cross sectional view of a blow molding apparatus after radially expanding the tube.

FIGS. 7(a) and 7(b) depict a schematic illustration of a blow molding system and process. As depicted in FIG. 7(a), a polymer tube 700 with an outside diameter 705 is positioned within a mold 710. A fluid, (conventionally a gas such as air, nitrogen, oxygen, argon, etc.) may then be conveyed into a proximal open end 730 of polymer tube 700 to increase the pressure in tube 700. A distal end 720 of tube 700 may be closed, but may be open in subsequent manufacturing steps. The fluid may be conveyed by a nozzle that runs through tube 700. A tensile force 735 may also be applied at proximal end 730 or distal end 720, or both.

As shown in FIG. 7(a), a mold 710 and tube 700 are heated by a nozzle 745 that directs a heated gas at mold 710, as shown by an arrow 750. Nozzle 745 translates along the longitudinal axis of mold 710, as shown by an arrow 755. The increase in pressure inside of polymer tube 700 facilitated by an increase in temperature of the polymer tube, causes radial deformation of polymer tube 700, as indicated by an arrow 740. FIG. 7(b) depicts polymer tube 700 in a deformed state with an outside diameter 715 within mold 710.

Thus, process parameters include, but are not limited to, pressure inside of the tube, temperature of the tube or temperature of heating fluid, and nozzle speed. In general, the higher temperature, pressure, and nozzle speed, the faster the expansion. It has been found that the fast expansion can result in formation of a blow molded tube with the bilayer structure.

In one embodiment, the temperature of the heating gas or the temperature of the tube during expansion is from about 180° F. to 300° F., more narrowly from about 200° F. to 260°

F., and even more narrowly from about 200° F. to 240° F. In one embodiment, the nozzle speed is about 0.1 to 3 mm/sec, from about 0.5 to 2.0 mm/sec, or from about 0.8 to 1.5 mm/second. In some embodiments, the nozzle speed is greater than 2 mm/sec. In one embodiment, a gas pressure in the tube during expansion is about 100 psi to 300 psi, more narrowly from about 140 to 250 psi, and even more narrowly from about 160 psi to 200 psi.

The polymeric tube can be heated prior to and/or contemporaneously with the deformation of the tube. For example, the temperature of the tube can be increased to a deformation temperature prior to deformation and maintained at the deformation temperature during deformation. The temperature of the tube can also be increased at a constant or nonlinear rate during deformation.

In some embodiments, the polymeric tube may be heat set after deformation to allow the polymer to rearrange upon deformation. "Heat setting" refers to allowing the polymer to equilibrate or rearrange to the induced oriented structure, caused by the deformation, at an elevated temperature. The pressure inside the tube, the tension along the cylindrical axis of the tube, and the temperature of the tube may be maintained above ambient levels for a period of time to allow the polymer tube to be heat set.

As indicated above, a stent may be crimped onto a delivery device so that the stent can be deployed upon insertion at an implant site. Generally, stent crimping involves affixing the stent to the delivery catheter or delivery balloon such that it remains affixed to the catheter or balloon until the physician desires to deliver the stent at the treatment site. The stent can be crimped by any suitable crimper. The delivery device that the stent may be crimped on can be a balloon-catheter assembly.

Although the preferable embodiment is a stent, the medical device may include any implantable medical device, such as stent-grafts and grafts. The stent is used to open a lumen within an organ in a mammal, maintain lumen patency, or reduce the likelihood of narrowing of a lumen.

The stent may be either partially or completely from biodegradable polymers. Polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and may be gradually absorbed and eliminated by the body. Biodegradation refers generally to changes in physical and chemical properties that occur in a polymer upon exposure to bodily fluids as in a vascular environment. The changes in properties may include a decrease in molecular weight, deterioration of mechanical properties, and decrease in mass due to erosion or absorption.

In one embodiment, the stent or the tube that is used to fabricate the stent may be formed from poly(L-lactide) (LPLA), poly(L-lactide-co-glycolide) (LPLG), or a blend thereof. In another embodiment, the tube or stent can be formed from a blend of LPLA or LPLG and a block copolymer LPLG-b-poly(glycolide-co-caprolactone) (LPLG-b-P(GA-co-CL)). In yet another embodiment, the tube for use in fabricating the stent includes bioceramic nanoparticles or fibers dispersed within the polymer, for example, calcium sulfate nanoparticles. In an exemplary embodiment, the tube is formed from LPLG-b-P(GA-co-CL) block copolymer mixed with calcium sulfate nanoparticles with the weight ratio at 100:10:1 (LPLG/P(GA-co-CL)/calcium sulfate). Other polymers may be used to fabricate the stent. For example, the stent may be made from a polymer that is selected from the group consisting essentially of poly(D,L-lactide); poly(L-lactide); poly(L-lactide-co-glycolide); or poly(D,L-lactide-co-glycolide).

Other representative examples of polymers that may be used to fabricate a stent coating include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(L-lactide-co-ϵ-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating a stent according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. The stents may also be metallic, low-ferromagnetic, non-ferromagnetic, biostable polymeric, biodegradable polymeric or biodegradable metallic.

It is also contemplated that the stent includes a drug, such as a drug coating on the luminal surface of the device. The drug, for example, may be used to further stimulate the development of an endothelial cell layer on the surface of the stent, thereby preventing restenosis as well as modulating the local chronic inflammatory response and other thromboembolic complications that result from implantation of the medical device. A bioactive agent may be, without limitation, antiproliferative, anti-inflammatory, antineoplastic, antiplatelet, anti-coagulant, anti-fibrin, antithrombonic, antimitotic, antibiotic, antiallergic, antioxidant and/or cytostatic.

EXAMPLES

The polymeric tubes described in the examples below were fabricated by radially expanding the polymeric tubes using parameters that result in formation of a rough outer surface. For example, the gas pressure in the tubes during expansion was from about 160 psi to 250 psi. The temperature of the tube during expansion was from about 240° F. to 400° F. The tubes were heated by translating a nozzle adjacent to the mold having a speed of about 2.0 mm/second.

Figure 8A:
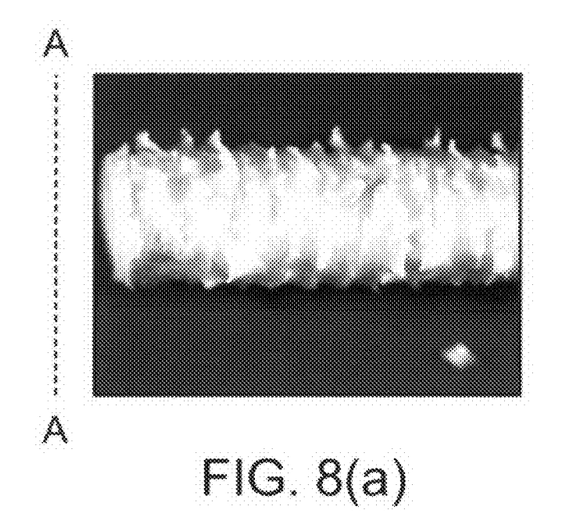
FIG. 8(a) is a photograph of an axial view of a tube having a rough luminal surface after undergoing degradation in a solution.

FIG. 8(a) is a photograph of an axial view of a tube made from a blend of LPLG/LPLG-co-P(GA-co-CL) block copolymer/dispersed calcium sulfate nanoparticles with the weight ratio at 100:10:1, having a non-smooth abluminal surface. The photograph shows an outer surface of the tube and was taken after 45 days of being immersed in phosphate buffer solution at 37° C.

Figure 8B:
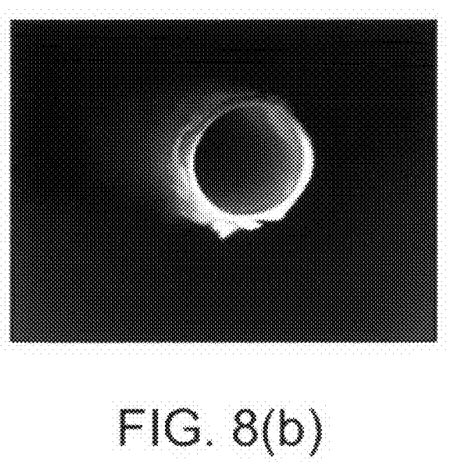
FIG. 8(b) is a photograph of a radial cross sectional view of the tube in FIG. 8(a).

FIG. 8(b) is a photograph of a radial cross sectional view of the tube in FIG. 8(a) taken along A-A.

Figure 9A:
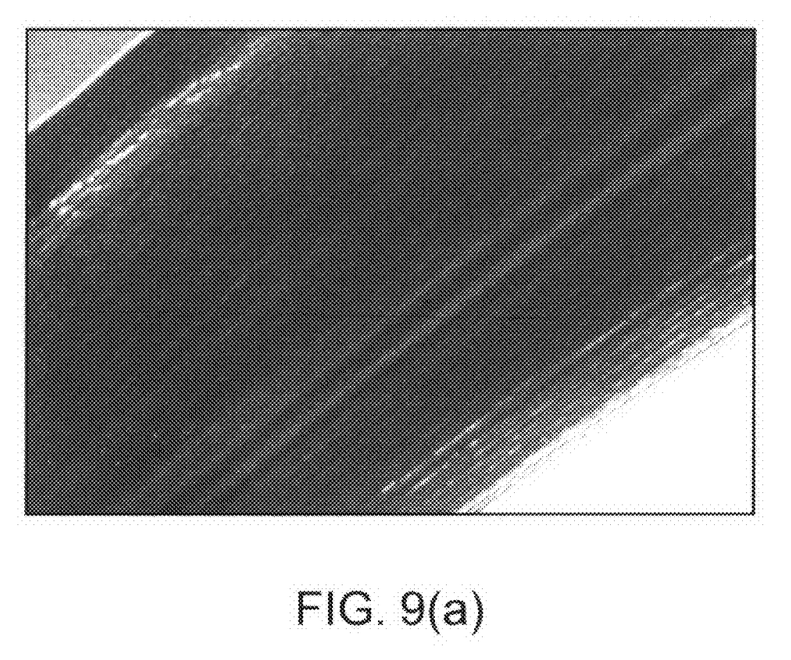
FIGS. 9(a) and 9(b) are photographs showing close-up views of an abluminal surface of the tube of FIG. 8(a) prior to immersion in the phosphate buffer solution.
Figure 9B:
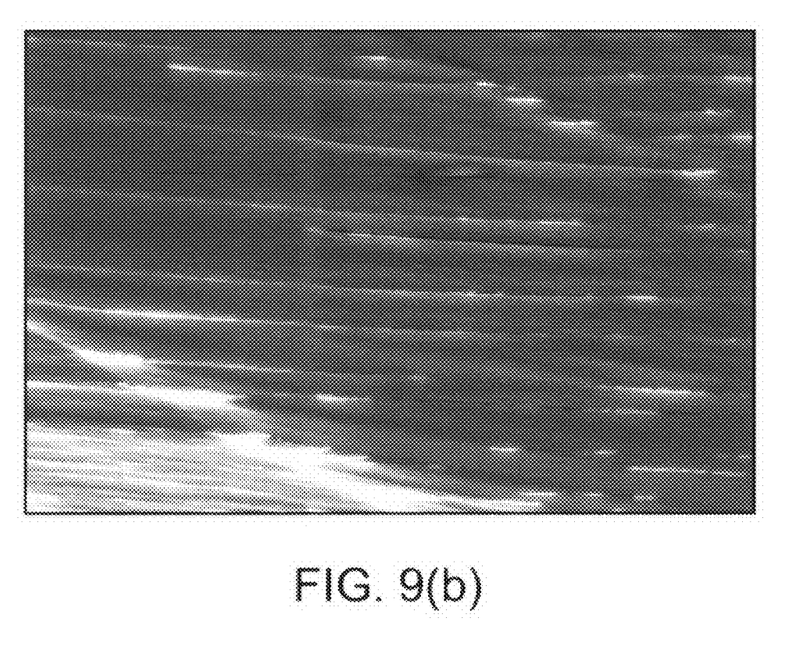

FIGS. 9(a) and 9(b) are photographs showing close-up views of an abluminal surface of the tube of FIG. 8(a) prior to immersion in the phosphate buffer solution.

While particular embodiments of the present invention have been shown and described, it will be obvious to those skilled in the art that changes and modifications can be made without departing from this invention in its broader aspects.

The invention claimed is:

1. A method of fabricating a stent, the method comprising:
   radially expanding a bioabsorbable polymer tube such that a majority of a luminal surface of the expanded tube is substantially smooth and a majority of an abluminal surface of the expanded tube is rougher than the luminal surface of the expanded tube;
   the rougher abluminal surface being formed by selection of process parameters capable of producing the rougher abluminal surface, including
      using a heating nozzle, heating the tube from about 180° F. to 300° F.,
      using a nozzle speed of about 0.1 mm/sec to 3.0 mm/sec, and
      using a gas for said radial expansion of the bioabsorbable polymer tube at a gas pressure of about 100 psi to 300 psi; and
   laser cutting a stent pattern into the expanded tube to fabricate a stent.

2. The method according to claim 1, wherein the abluminal surface of the expanded tube has a roughness factor that is greater than 1.5 times a roughness factor of the luminal surface of the expanded tube.

3. The method according to claim 1, wherein a degradation rate at an abluminal surface of the stent is greater than a substantially smooth surface upon exposure to bodily fluids.

4. The method according to claim 1, wherein an abluminal surface of the stent promotes endothelial cell growth more than a substantially smooth surface.

5. The method of claim 1, wherein the process parameters are 160 psi to 250 psi, 240° F. to 250° F. and the nozzle speed is about 2 mm/sec.

6. A method of fabricating a stent, the method comprising:
   radially expanding a polymeric tube by increasing a pressure in the tube and heating the tube, wherein the pressure in the tube during expansion is from about 120 psi to 250 psi, wherein the temperature of the tube during expansion is from about 200° F. to 300° F., and wherein the tube is disposed in a mold and heated by axially translating a nozzle along the mold, the nozzle directing a heated gas at the mold, wherein the nozzle is translated at a rate of 1.0 mm/second to about 3 mm/second; and
   laser cutting a stent pattern into the expanded polymeric tube to fabricate a stent, the stent having a substantially smooth luminal surface and a rough abluminal surface.

7. The method according to claim 6, wherein a surface area of the abluminal surface of the stent is at least 1.5 times greater than a surface area of the luminal surface of the stent.

8. The method according to claim 6, wherein the abluminal surface of the stent promotes endothelial cell growth more than a substantially smooth surface.

9. The method according to claim 6, wherein a degradation rate at the abluminal surface of the stent is greater than a substantially smooth surface upon exposure to bodily fluids.

10. The method according to claim 6, wherein the stent comprises a blend including a majority of LPLA or LPLG and LPLG-b-P(GA-co-CL), wherein a plurality of bioceramic particles are dispersed within the blend.

11. The method according to claim 6, further comprising coating the cut stent with a biodegradable coating.

12. The method according to claim 11, wherein the coating includes fibers, nanoparticles, or a blend thereof.

13. The method according to claim 6, wherein the polymeric stent consists essentially of LPLA or LPLG.

14. The method according to claim 6, wherein the abluminal surface of the stent has a roughness effective to stimulate the adherence of endothelial cells to the abluminal surface of the stent, thereby forming a layer of mature endothelial cells on the abluminal surface of the stent.

* * * * *